(12) United States Patent
Tu (10) Patent No.: US 6,836,678 B2
(45) Date of Patent: Dec. 28, 2004

(54) NON-INVASIVE BLOOD GLUCOSE MONITOR

(76) Inventor: Xiang Zheng Tu, 1293 Westwood St., Redwood City, CA (US) 94061

( * ) Notice: Subject to any disclaimer, the term of this patent is extended or adjusted under 35 U.S.C. 154(b) by 19 days.

(21) Appl. No.: 10/368,813

(22) Filed: Feb. 13, 2003

(65) Prior Publication Data

US 2004/0162470 A1 Aug. 19, 2004

(51) Int. Cl.$^7$ ................................................. A61B 5/00
(52) U.S. Cl. ........................ 600/316; 600/365; 600/310
(58) Field of Search ................................. 600/316, 365, 600/473, 309–310

(56) References Cited

U.S. PATENT DOCUMENTS

| | | | |
|---|---|---|---|
| 4,169,676 A | | 10/1979 | Kaiser |
| 4,655,225 A | | 4/1987 | Dahne et al. |
| 5,413,108 A | * | 5/1995 | Alfano .................. 600/478 |
| 5,424,545 A | | 6/1995 | Block et al. |
| 5,748,308 A | * | 5/1998 | Lindberg et al. ........... 356/310 |
| 5,782,755 A | | 7/1998 | Chance et al. |
| 5,974,337 A | | 10/1999 | Kaffka et al. |
| 6,031,233 A | | 2/2000 | Levin et al. |
| 6,064,898 A | | 5/2000 | Aldrich |
| 6,442,411 B1 | * | 8/2002 | Guthermann ............. 600/322 |
| 2003/0040683 A1 | * | 2/2003 | Rule et al. ............... 600/584 |
| 2003/0209669 A1 | * | 11/2003 | Chou ..................... 250/343 |
| 2003/0225321 A1 | * | 12/2003 | Cote et al. ............... 600/318 |

OTHER PUBLICATIONS

Webster's II New Riverside University Dictionary, Riverside Publishing Company, 1994, p. 766, 1116.*

* cited by examiner

Primary Examiner—Eric F. Winakur
Assistant Examiner—Matthew Kremer
(74) Attorney, Agent, or Firm—Bruce H. Johnsonbaugh (57) ABSTRACT

A micro-optical-mechanical-electro-system (MOMES)-based non-invasive blood glucose monitor comprises a micromachined infrared optical filter array, a micromachined infrared mechanical modulator array, at least one micromachined infrared tunable filter, and at least one infrared detector. Each optical filter is aligned with a mechanical modulator along its optical axis direction. The optical filter continuously divides a monochromatic infrared light in a wavelength range within 0.8 to 25 micron from an infrared light. The aligned mechanical modulator turns the monochromatic infrared light into an alternating monochromatic infrared light. The tunable filter is aligned with the infrared detector along its optical axis direction. The tunable filter selects the back-diffused alternating monochromatic infrared light emitted from a measured blood subject that is illuminated by the alternating monochromatic infrared light. The infrared detector converts the back-diffused alternating monochromatic infrared light into an alternating electronic signal. Then a photo-integrated circuit (IC) combines with the infrared detector for synchronous detection and amplification of the electronic signal generated by the synchronous detection.

22 Claims, 10 Drawing Sheets

NON-INVASIVE BLOOD GLUCOSE MONITOR

FIELD OF THE INVENTION

This invention is generally related to a non-invasive blood glucose monitor, and more particularly to a non-invasive blood glucose monitor based on micro-optical-mechanical-electro-system (MOMES).

BACKGROUND OF THE INVENTION

Non-invasive measurement of blood glucose concentration offers many advantages over invasive measurements, since the intermittent tests, which are widely practiced by diabetic patients, involve pain and discomfort from frequent finger-pricking.

Non-invasive measurement approaches of blood glucose concentration based on absorption measurements in the infrared region have been explored more than 20 years.

An early U.S. Pat. No. 4,169,676 (October, 1979) to Kaiser shows a method for the use of attenuated total reflection glucose measurement by placing the attenuated total reflection plate directly against the skin and especially against the tongue. The procedure and device shown there uses a laser and determines the content of glucose in a specific living tissue sample by comparing the infrared absorption of the measured material against the absorption of infrared in a control solution by use of a reference prism.

Another early U.S. Pat. No. 4,655,225 (April, 1987) to Dahne, et al. describes an apparatus for non-invasively measuring the level of glucose in a blood stream or tissues. The method is photometric and uses light in the near-infrared region. Dahner's device is jointly made up to two main sections, a light source and a detector section. They may be situated about a body part such as a finger. The desired near-infrared light is achieved by use of filters. The detector section is made up of a light-collecting integrating sphere or half-sphere leading to a means for detecting wavelengths in the near-infrared region.

In recent years more methods and apparatus have been proposed. U.S. Pat. No. 5,974,337 (Oct. 26, 1999) describes an instrument for non-invasive glucose measurement. The described instrument irradiates the distal phalanx of a subject's finger with light in the near infrared. The transmitted or reflected radiation is detected and analyzed and an estimate of blood glucose level made. The signal is coupled with a fiber optic probe by means of a conventional arrangement of lenses and mirrors. Illumination fibers and collection fibers are provided in separate structures.

U.S. Pat. No. 5,424,545 (Jun. 13, 1995) describes an instrument for non-invasive blood analyte determination that relies on calorimetric analysis to arrive at a blood analyte determination. A light beam is coupled with an illumination fiber by means of lenses and mirrors.

U.S. Pat. No. 6,064,898 (May 16, 2000) describes a non-invasive blood component analyzer that provides built-in path length monitoring to allow use in subjects of varying finger size. It provides a light source either from LED's or from a lamp. The light is simply emitted in the vicinity of the sampling site and coupled through the atmosphere.

U.S. Pat. No. 5,782,755 (Jul. 21, 1998) discloses a method of spatial resolved diffused reflectance for measurement of glucose in a biological system. It uses multiple spot sources, such as flash bulbs, and a single detector. The light sources are spaced different distances along a single line from a detector and are sequenced at different time intervals to derive the spatial reflectance profiles.

All above-mentioned methods and apparatus are impossible to detect on the spectrum the relative heights of the waveform (peak and trough), which are finely varied by the coupling of glucose and protein, resulting in insufficiency in the accuracy and reproducibility of the blood glucose measurement.

U.S. Pat. No. 6,031,233 (Feb. 29, 2000) describes an apparatus based on an infrared spectrometer. Light is emitted from a lamp and passed through an acousto-optical tuning filter for wavelength selection. The acoustic-optical tuning filter is composed of a high frequency electric power source, a high frequency vibrator, and an acousto-optic variable oscillator. The filtered light is focused through one or more lenses and directed toward the measurement site through a window. The use of the acousto-optical tuning filter for wavelength selection requires a wavelength synthesizer and an RF amplifier.

This apparatus is not only complicated and expensive but also leaves several problems to be solved.

Problem 1, the light absorbed by the tissue subjected to analysis constitutes, together with other losses due to scattered stray radiations and RF interference, signals inherent to the practice of the method and the apparatus components, the background response noise from which the useful signals must be separated.

Problem 2, skin tissue is composed of various compositions of fat and protein, as well as veins, arteries, and bones. Such heterogeneous structure can contribute to local variation of the light absorption and scattering.

Problem 3, a temporal variation in glucose concentration is associated with blood flow changes during a heartbeat process of the blood subject of measurement. Data received at individual points of the heartbeat process are not the same.

Problem 4, portable and handheld non-invasive blood glucose instruments are demanded for point of care and in home use. Such instruments in which light is coupled by means of an arrangement of conventional lenses and mirrors have high space requirements and they are highly vulnerable to mechanical shock.

SUMMARY OF THE INVENTION

Accordingly, it is intended to provide a non-invasive blood glucose monitor of solving the aforementioned problems, excelling in accuracy and reproducibility.

It is an object of the present invention to provide a non-invasive blood glucose monitor with main components being MOMES devices so that it is small enough to fit the palm of your hand.

Furthermore, it is an object of the present invention to provide a non-invasive blood glucose monitor that enables to use a combination of modulated monochromatic infrared light and synchronous detection technology for maximizing the electronic single-to-noise ratio.

It is yet another object of the present invention to provide a non-invasive blood glucose monitor that enables the use of a tunable filter to eliminate stray infrared radiation so that the optical signal to noise ratio can be maximized.

It is yet another object of the present invention to provide a non-invasive blood glucose monitor that enables selecting and switching of the illumination infrared light in an infrared wavelength range so that an infrared absorbance spectrum of the blood subject of measurement can be obtained.

It is yet another object of the present invention to provide a non-invasive blood glucose monitor that enables scanning over a large area of measurement so that the poor reproducibility caused by non-homogeneity of the subject of measurement can be overcome.

It is yet another object of the present invention to provide a non-invasive blood glucose monitor that enables the measurement of blood glucose in a period of a heartbeat and an average can be made to eliminate the blood flow changes due to heartbeat.

In order to realize the above-mentioned objects, the present invention provides a MOMES-based non-invasive blood glucose monitor consisting primarily of a micromachined infrared interferometer array, a micromachined infrared mechanical modulator array, a micromachined infrared tunable filter, and needed driver and signal processing integrated circuits.

The micromachined infrared interferometer array, micromachined infrared mechanical modulator array, and micromachined infrared tunable filter are an adaptation of Fabry-Perot devices that employ the principle of optic interference. The basic unit is a Fabry-Perot cavity consisting of two parallel planar reflectors separated by an air gap. At least two flexible beams support one of the two reflectors. Applying a voltage to the two reflectors can change the length of the air gap.

Infrared light passes through one of the two reflectors and is multiply reflected within the cavity. The multiply transmitted light beams interact with each other creating optical interference effects, which result in the transmission, through the other reflector, of only one particular wavelength and its harmonics.

The MOMES is a device that is, in general, built using micromaching and standard integrated circuit techniques. Starting with a silicon wafer and depositing a series of films such as nitrides, polysilicon, oxides and metals, one builds a complex three-dimensional structure in much the same way one builds an integrated circuit. However, unlike integrated circuits, one then releases the device by etching away the oxides, producing a structure that can move. This subtle change in processing allows one to produce optical devices that move, including data modulators, variable attenuators, optical switches, active equalizers, add/drop multiplexers, optical cross-connects, dispersion compensators, all-optical switches, filters, tunable laser sources, active packages and adaptive optical elements.

The micromachined infrared interferometer array and micromachined infrared detector are mounted on the surface of a substrate and the micromachined infrared mechanical modulator array and micromachined infrared tunable filter are mounted on the surface of another substrate. The substrates may incorporate three driver circuits and a photo-integrated circuit. The monitor further consists of at least one infrared thermal radiator, at least one collimator, a band pass infrared filter, an electronic filter, an A/D converter, a microprocessor, and a display.

In operation of the monitor, an infrared light source irradiates an infrared light. The infrared light passes through a band pass filter that covers a wavelength range within 0.8 to 2.5 $\mu$m or 2.5 to 25 $\mu$m. An actuated micromachined interferometer divides a monochromatic infrared light from the filtered infrared light. An actuated mechanical modulator converts the monochromatic infrared light into an alternating monochromatic infrared light. The alternating infrared light illuminates a first portion of a blood subject of measurement. A back-diffused alternating infrared light from the first portion of the blood subject of measurement passes through the actuated micromachined tunable filter. The infrared detector converts the filtered back-diffused alternating infrared light into an alternating electronic signal. After amplification the alternating electronic signal is demodulated and converted into a digital signal. A microprocessor is used to process the digital signal for producing the data of the first portion of the blood subject. In the same way the rest of the micromachined interferometers and mechanical modulators are actuated in turn for producing the blood glucose data of the other portions of the blood subject. Again in the same way a plurality of monochromatic infrared lights each with a central wavelength are divided from the infrared light and each monochromatic infrared light is used to repeat the above-mentioned steps for collecting a corresponding blood glucose data of the blood subject.

The foregoing monitor offers a number of advantages. Since the monitor is based on MOMES, it can be made small enough to fit into the palm of your hand. It allows using mature microelectronic technology for batch-production so that the production cost can be reduced substantially. It permits the infrared light being passively aligned where the optics structure of the monitor can be expected to be compact and reliable. It allows using synchronous detection so that high electronic signal to noise ratio can be obtained. Its tunable filter can eliminate stray infrared so that the optical signal to noise ratio can be maximized. In addition, it allows averaging of back-diffused infrared light over a large area of the blood subject. Such averaging reduces any non-homogeneity of the illumination structure in the tissue and thus improves reproducibility and reliability of the measurements.

DETAILED DESCRIPTION OF THE INVENTION

Figure 1:
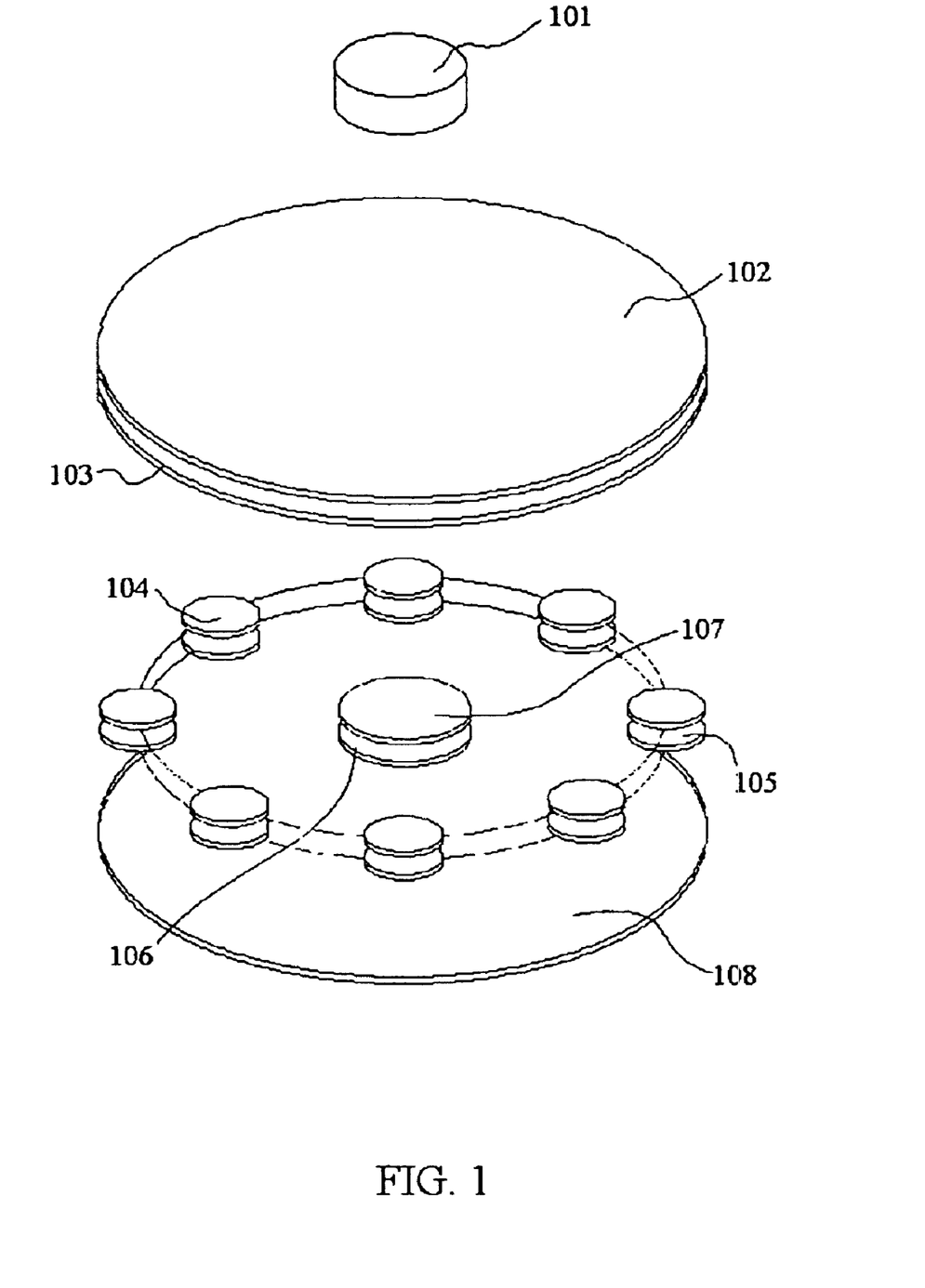
FIG. 1 is a perspective view of a simplified non-invasive blood glucose monitor according to the present invention.

According to the present invention, a MOEMS-based, non-invasive blood glucose monitor as shown in FIG. 1, comprises an infrared light source 101, a collimator 102, an infrared narrow band filter 103, a micromachined infrared optical filter array 104, a micromachined infrared mechanical-modulator array 105, a micromachined infrared tunable filter 106, and an infrared detector 107.

The collimator 102 makes the infrared light irradiated from the infrared source light 101 run parallel to its optical axis. The infrared narrow-band filter 103 only enables the infrared light with the wavelengths ranged in a narrow spectral band to pass through. An actuated micromachined infrared optical filter 104 further enables a monochromatic infrared light with a predetermined single wavelength to pass through. An actuated micromachined infrared mechanical modulator 105 that is aligned with the actuated micromachined optical filter 104 turns the monochromatic infrared light into an alternating monochromatic infrared light. Then the alternating monochromatic infrared light illuminates a portion of the surface of a blood subject of measurement 108. The actuated micromachined infrared tunable filter 106 selects the back-diffused alternating monochromatic infrared light that is generated due to the reaction between the incident alternating monochromatic infrared light and the blood subject of measurement and enables it to pass through. The infrared detector 107 converts the back-diffused alternating monochromatic infrared light into an alternating electronic signal.

The optical filters of the micromachined infrared optical filter array 104 are in turn actuated so that each optical filter can divide a monochromatic infrared light. Correspondingly, the modulators of the micromachined infrared mechanical modulator array 105 are also in turn actuated so that each modulator turns an incident monochromatic infrared light into an alternating monochromatic infrared light. Because of this the alternating mono-chromatic infrared light can scan the surface of the blood subject of measurement. The wavelengths of the alternating monochromatic infrared light can be changed so that a desired infrared spectral response in a predetermined wavelength range can be obtained.

The infrared source 101 can be a thermal radiator or a semiconductor radiator. One type of thermal radiator utilizes metal wire or metal foil sources, such as miniature lamps, radiators in TO-packages or glass bulbs. Another type of thermal radiator utilizes thin film sources or thick film sources. Since the thermal radiator's temperature, its emissivity and area determine the radiation power released, it is preferred to use the first type as a near-infrared source and the second type as a mid-infrared source.

Figure 2:
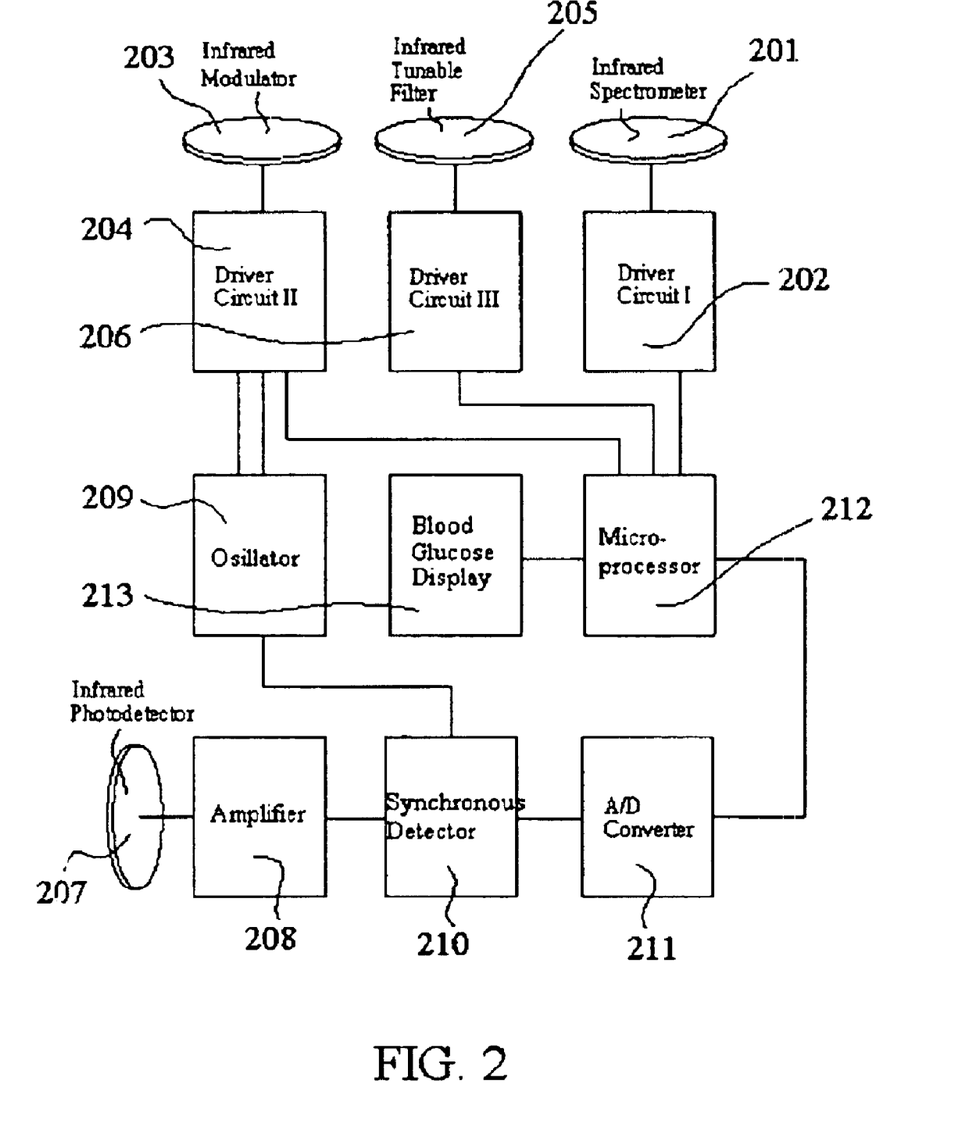
FIG. 2 is a block diagram illustrating an electronic configuration of a non-invasive blood glucose monitor according to the present invention.

The electrical and electronic configuration of the non-invasive blood glucose monitor, according to the present invention, is shown in FIG. 2. The non-invasive blood glucose monitor is controlled by a microprocessor 212. The microprocessor issues data to three driver circuits 202, 204, and 206, respectively. Then driver circuits 202, 204, and 206 actuate a spectrometer 201, a modulator 203, and a tunable filter 205, respectively. The modulator 203 is controlled by an oscillator 209. An alternating electronic signal generated by an infrared detector 207 is amplified by a preamplifier 208. The amplified alternating electronic signal is detected by a synchronous detector 210. The oscillator 209 also is connected to the synchronous detector so the synchronous detection can be realized. The output of the synchronous detector 210 is further processed by an A/D converter 211. The microprocessor 212 processes the received digital signals and produces an infrared absorbance spectrum. After analyzing the infrared absorbance spectrum by the microprocessor 212, a fine result is displayed by a blood glucose display 213.

Figure 3A:
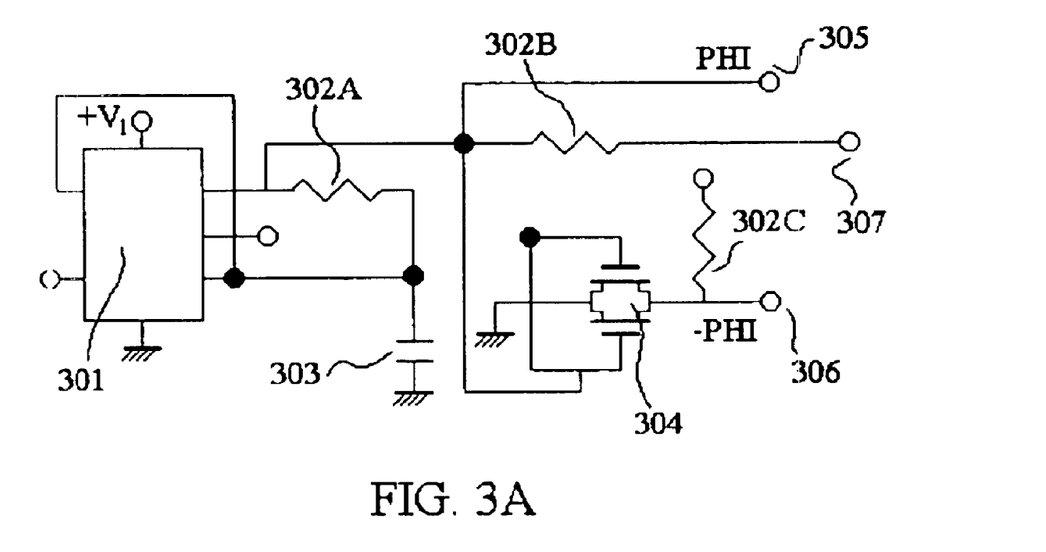
FIG. 3A shows a detailed circuit of the oscillator of the FIG. 2.

An oscillator is shown in FIG. 3A. It forms by a CMOS timer 301, a CMOS quad bilateral switch 304, three resistors 302A, 302B, and 302C, and a capacitor 303. The oscillation frequency and duty cycle of the oscillator can be accurately set by two external resistors and one capacitor. An output port 307 is connected to the micromachined infrared mechanical modulators 203 of FIG. 2, which sends out a signal for turning the monochromatic infrared light into an alternating monochromatic infrared light. Other two output ports 305 and 306 send out signals PHI and −PHI, respectively, which are 180 degrees out of phase.

Figure 3B:
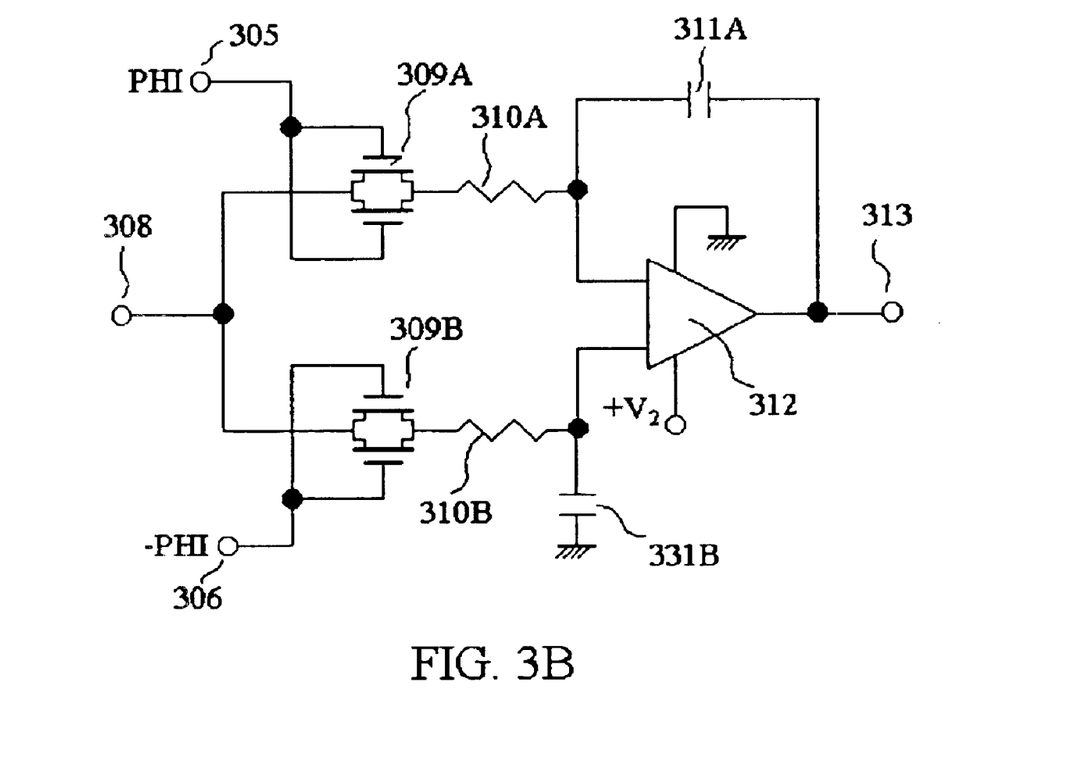
FIG. 3B shows a detailed circuit of the synchronous detector of the FIG. 2.

A synchronous detector is shown in FIG. 3B. It forms by two CMOS quad bilateral switches 309A and 309B, a CMOS quad low power operational amplifier 312, two resistors 310A and 310B, and two capacitors 311A and 311B. Input port 308 receives the alternating electronic signal from the preamplifier 208 of FIG. 2. Other two input ports 305 and 306 receive signals PHI and −PHI for driving two quad bilateral switches 309A and 309B, respectively. The operational amplifier 312 demodulates the alternating electronic signal so that the signals that are at the same frequency as the PHI and −PHI are integrated, and others are rejected.

Figure 4A:
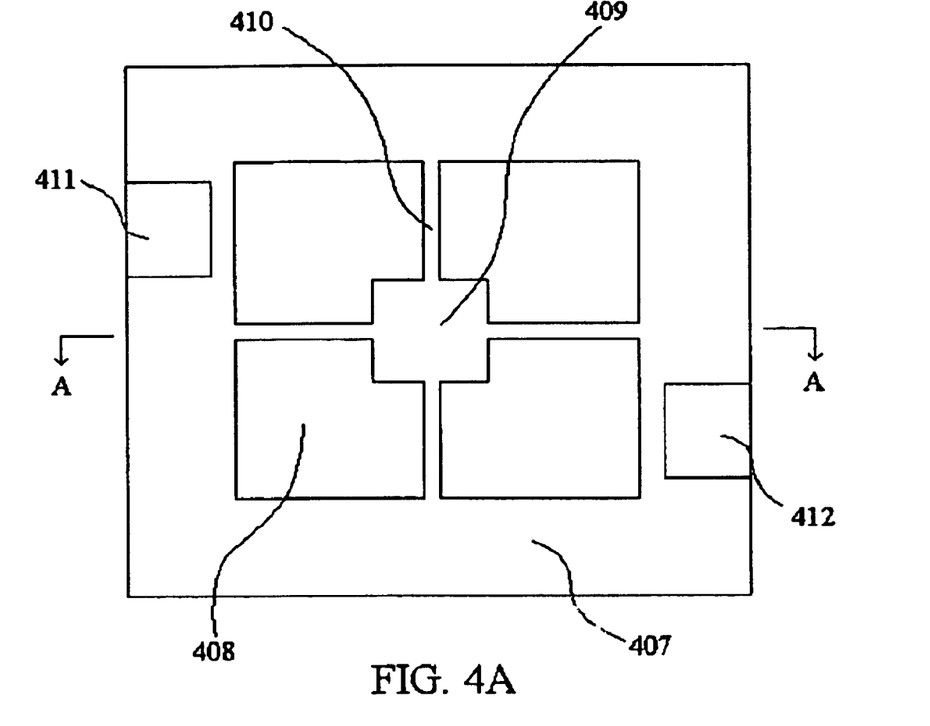
FIGS. 4A and 4B show the top view and cross-sectional view of a micromachined Fabry-Perot cavity that is defined by two parallel planar reflectors, respectively, according to the present invention.
Figure 4B:
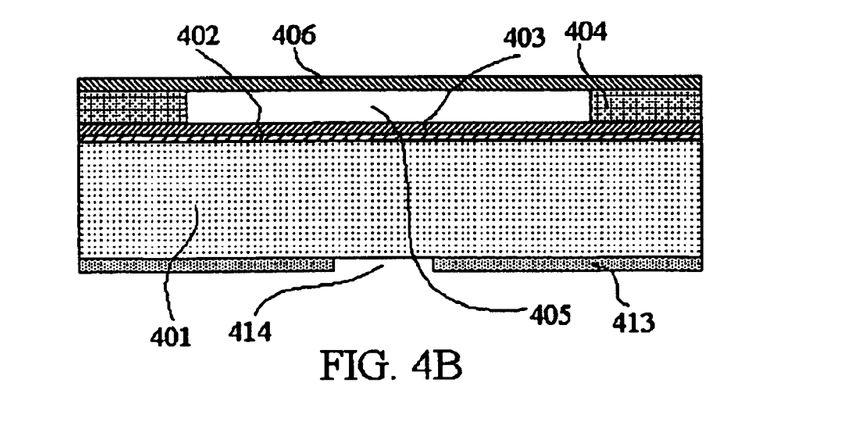

The micromachined infrared optical filter array 104, micromachined infrared mechanical modulator array 105, and micromachined infrared tunable filter 106 of FIG. 1, are based on variable air gap Fabry-Perot cavities. A typical variable air gap Fabry-Perot cavity, as shown in FIGS. 4A and 4B, mainly consists of a deformable structure 406, two parallel planar mirrors 403 and 409 that sandwich an air gap 405 there between, and an anti-reflecting layer 402. The cavity is disposed on a substrate 401 that has two bonding pads 411 and 412, a back infrared light blocking layer 413, and a back infrared light window 414 thereon. The deformable structure 406 includes a central pad that is acted as the reflecting mirror 409 and four side cantilever beams 410 that are suspended over trenches 408. The deformable structure 406 is supported by a frame 407 that surrounds the whole cavity. The air gap 405 is created by selectively etching the central portion of a separating layer 404. The cavity further consists of two electrodes that are preferred to be the two reflecting mirrors themselves. As an alternative, the electrodes can be formed by additional layers and preferably located adjacent to the air gap 405 so that the cavity is easy to be actuated by an electrostatic force.

It is preferable that the deformable structure 406, reflecting mirrors 403 and 409 are created from a polysilicon layer, the anti-reflecting layer 402 is made of silicon nitride ($Si_3N_4$), and the separating layer 404 is made of silicon dioxide ($SiO_2$). The polysilicon layer can be replaced by a $Si_3N_4$ layer formed by low-pressure vapor chemical deposition (LPCVD) or an amorphous silicon carbine (SiC) layer formed by plasma enhanced vapor chemical deposition (PECVD). All these materials are transparent in the infrared spectral range.

The thickness of the deformable structure 406 is preferred to be equal to an odd multiple of $\lambda_0/4n$, where $\lambda_0$ is the infrared wavelength and n is the refractive index so that it can be considered as a construction part of a multi-layered dielectric mirror or a distributed Bragg reflector (DBR).

The thickness of the separating layer 404 determines the length of the air gap 405. The static length of the air gap 405 is preferred to be equal to an odd multiple of $\lambda_0/4$, so that after deformation the length can reach an even multiple of $\lambda_0/4$.

Doped polysilicon can be used to create the electrodes. As an alternative, the electrodes are made of Sn-doped $In_2O_3$ (ITO) that is transparent in the infrared spectral range. ITO is commonly etched with HCl solution. Since HF solution that is used to etch the $SiO_2$ layer does not attack ITO, for the $Si_3N_4$ layer formed by PECVD, $SiO_2$ still can be used to form separating layer 404. It should be noted that in this case the sidewalls of the deformable structure 406 need to be protected during the etch process of the separating layer 404. The thickness of the electrodes is preferred to be equal to $\lambda_0/4n$, so that the electrodes can be considered as a construction part of a multi-layered dielectric mirror.

The reflecting mirrors 403 and 409 can be multi-layered dielectric mirrors or DBRs, which is a stack of alternating layers of higher refractive index and lower refractive index materials. The thickness of each layer is equal to $\lambda_0/4n$. The stack can be $Si_3N_4(1.94)/SiO_2(1.47)$, or $TiO_2(2.34)/SiO_2(1.47)$, or $Si(93.45)/SiO_2(1.47)$. The period number of the stack depends upon a desired reflectivity of the DBR mirrors. For $Si_3N_4/SiO_2$, $TiO_2/SiO_2$, and $Si/SiO_2$, which can be chosen in the range of 8 to 12, 4 to 6, and 1 to 2, respectively.

As an alternative, hybrid mirrors each consisting of a silicon layer or a silicon nitride layer coated with a thin gold or silver layer thereon can be used to form the reflecting mirrors 403 and 409. Gold and silver are not transparent in the infrared spectral range, so the thickness of the gold and silver layers is limited to be lower than 500 Å so that the absorption loss of the infrared rays is not too high.

A fabrication process for the typical cavity starts with preparing a silicon substrate. Then the deposition of an anti-reflecting layer consisting of wet $SiO_2$ and PECVD $Si_3N_4$ is performed. After opening a substrate contact hole through the anti-reflecting layer, a thick LPCVD polysilicon layer is deposited and structured by plasma etching. This conductive layer serves as the bottom mirror and the bottom electrode. The next step is the deposition of a LPCVD phosphorus deposed silicon dioxide (PSG) layer. The layer is structured in buffered HF solution. Then the second LPCVD polysilicon layer is deposited. Another PSG layer is deposited for doping the polysilicon layer. To release the internal stress and to drive in the dopants, an appropriate annealing step is performed at 1050° C. After removal of the doped PSG layer the top polysilicon layer is plasma structured. Then a portion of the separating layer is etched in HF solution to obtain a freestanding polysilicon structure. Finally a thick aluminum layer is evaporated and structured for contact lines and bonding pads.

As an alternative, a glass plate is used as a substrate. In this case a low temperature process is carried out, in which all fabrication steps are performed at a temperature not higher than 350° C. This limitation can be kept by using low temperature thin film deposition technologies, such as a PECVD, electron beam evaporation, and sputtering and PECVD amorphous silicon, PECVD silicon nitride, PECVD amorphous silicon carbine, and sputtered ITO are used to form the cavity.

When DBRs are used as the reflecting mirrors and they are made of a stack of $Si_3N_4/SiO2$ or $TiO_2/SiO_2$, the mirror pattern can be formed by a lift-off process. To this end, the pattern is first defined on the substrate using photoresist, such as an AZ3612 photoresist. A stack of $Si_3N_4/SiO_2$ or $Si/SiO_2$ is then blanket-deposited all over the substrate, covering the photoresist and areas in which the photoresist has been cleared. During the actual lifting-off, the photoresist under the film is removed with acetone, taking the film with it, and leaving only the film that is deposited directly on the substrate.

Before creating the air gap of the cavity, the sidewalls of the formed deformable structure and the top-reflecting mirror should be protected. To do this, another lift-off process can be performed so that a metallic film such as a gold film covers the sidewalls of the formed deformable structure and the top-reflecting mirror.

Figure 5A:
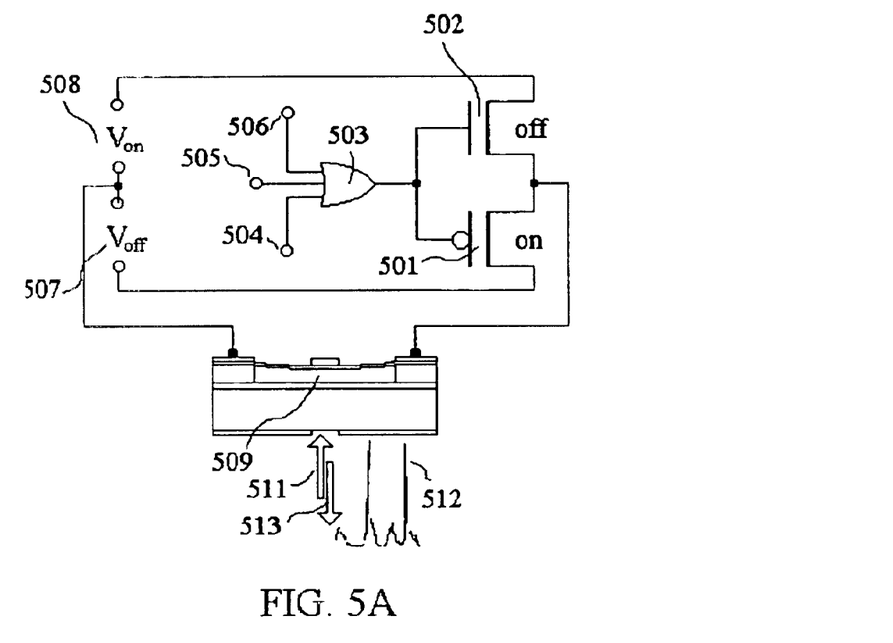
FIG. 5 shows the operation of a micromachined Fabry-Perot cavity acted as an infrared spectrometer or an infrared tunable filter, according to the present invention.
Figure 5B:
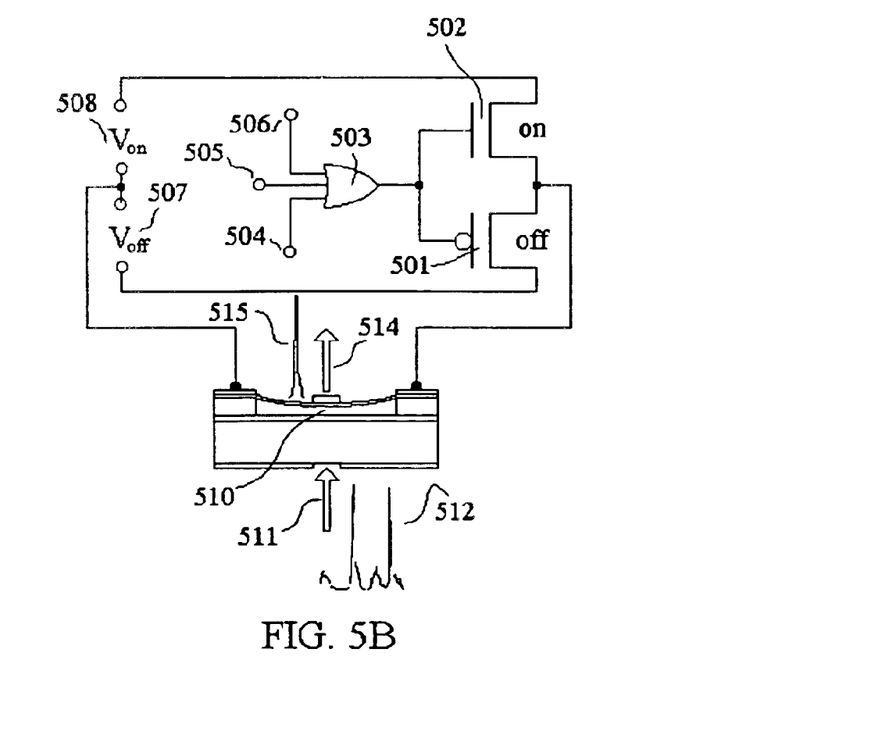

When the Fabry-Perot cavity is operated as an infrared optical filter or infrared tunable filter, the control and driver circuit is shown in FIG. 5A and FIG. 5B. The control and driver circuit preferably comprises the following components: a CMOS switch consisting of an n-MOS transistor 501 and a p-MOS transistor 502, an AND gate 503, a DC power $V_{off}$ 507, a DC power $V_{on}$ 508, and a cavity 509. The AND gate receives an address signal 504, an action signal 505, and a sequence control signal 506.

As the output of the AND gate 503 is "0", the n-MOS transistor 501 is "on" and the p-MOS transistor 502 is "off" so that the DC power $V_{off}$ is applied to the cavity 509. Since the two electrodes of the cavity form a capacitor, the applied voltage creates an electrostatic force that attracts the deformable structure toward the substrate surface. The attractive electrostatic force is finally balanced by the elastic force from the deformable structure. Therefore, the effective length of the air gap of the cavity is shortened with the applied voltage. The DC power $V_{off}$ 507 is adjusted to reach a value so that the effective length of the air gap of the cavity exactly equals to an odd multiple of $\lambda/4$. In this case the cavity is set on "off" state, or completely reflection state. As shown in FIG. 5A, an infrared light 511 with wavelengths ranging in a narrow band 512 is normally projected onto the window of the back of the cavity 509. Since the cavity 509 is on the "off" state, an infrared beam 513 is reflected back from the cavity 509.

As the output of the AND gate 503 is "1", the n-MOS transistor 501 is "off" and the p-MOS transistor 502 is "on" so that the DC power $V_{on}$ is applied to the cavity 510. The DC power $V_{on}$ 508 is adjusted to reach a value so that the effective length of the air gap of the cavity exactly equals to an odd multiple of $\lambda_0/4$. In this case the cavity is set on "on" state, or completely transmission state. As shown in FIG. 5B, an infrared light 511 with wavelengths ranging in a narrow band 512 is normally projected onto the window of the back of the cavity 509. Since the cavity 509 is on the "on" state, an infrared light 514 is comes out from the cavity 509. It should be noted that the infrared light 514 has converted into a single wavelength infrared light or a monochromatic infrared light 515.

Figure 6A:
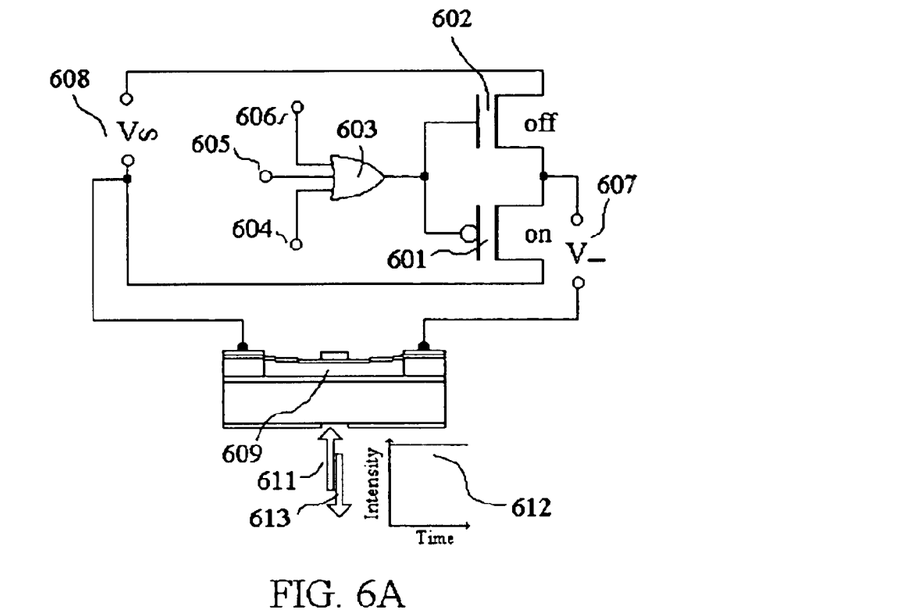
FIG. 6 shows the operation of a micromachined Fabry-Perot cavity acted as an infrared mechanical modulator, according to the present invention.
Figure 6B:
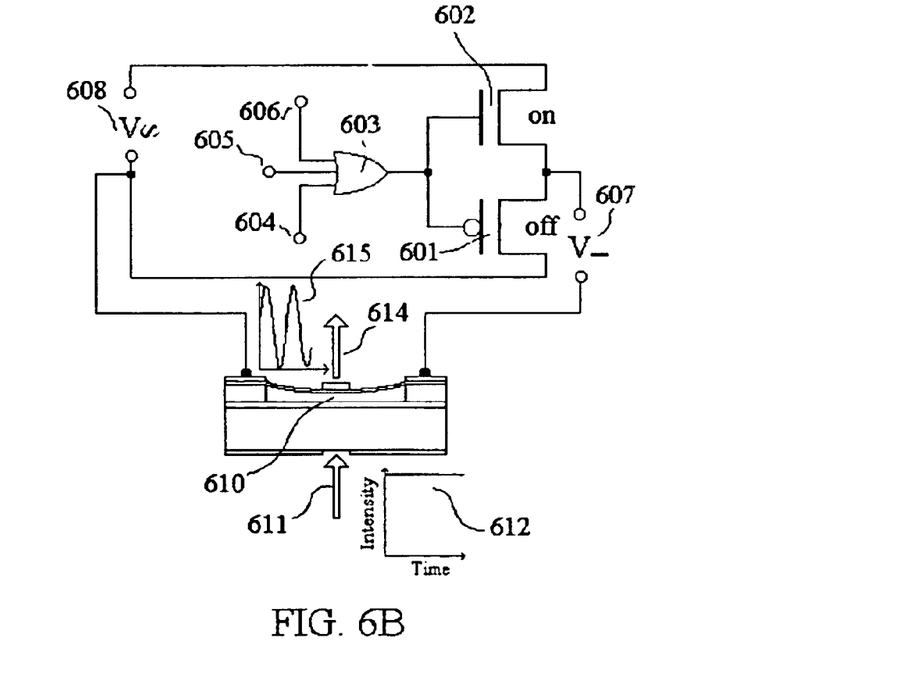

When the Fabry-Perot cavity is operated as an infrared mechanical modulator, the control and driver circuit is shown in FIG. 6A and FIG. 6B. The control and driver circuit preferably comprises the following components: a CMOS switch consisting of an n-MOS transistor 601 and a p-MOS transistor 602, an AND gate 603, a DC power signal $V_-$ 607, an AC power signal $V_-$ 608, and a cavity 609. The AND gate receives an address signal 604, an action signal 605, and a sequence control signal 606.

As the output of the AND gate 603 is "0", the n-MOS transistor 601 is "on" and the p-MOS transistor 602 is "off"

so that the DC power $V_-$ 607 is applied to the cavity 609. The DC power $V_-$ 507 is adjusted to reach a value so that the effective length of the air gap of the cavity exactly equals to an odd multiple of $\lambda_0/4$. In this case the cavity is set on "off" state, or completely reflection state. As shown in FIG. 6A, a monochromatic infrared light 611 with a constant intensity 612 is normally projected onto the window of the back of the cavity 609. Since the cavity 609 is on the "off" state, a monochromatic infrared light 613 is reflected back from the cavity 609.

As the output of the AND gate 603 is "1", the n-MOS transistor 601 is "off" and the p-MOS transistor 602 is "on" so that both the DC power $V_{on}$ 608 and the AC power $V_-$ 608 are applied to the cavity 610. The added AC power $V_-$ 608 is adjusted to reach a value so that the effective length of the air gap of the cavity can be varied from an even multiple of $\lambda/4$ to an adjacent odd multiple of $\lambda/4$. In this case the cavity is set on "modulation" state, or alternatively change state between a completely reflective state and a completely transmission state. As shown in FIG. 6B, a monochromatic infrared light 611 with a constant intensity 612 is normally projected onto the window of the back of the cavity 609. Since the cavity 609 is on the "modulation" state, a monochromatic infrared light 614 is comes out from the cavity 610. It should be noted that the incident monochromatic infrared light 611 has converted into a monochromatic infrared light 614 with an alternating intensity 615.

It should be noted that all the power signals $V_{on}$, $V_{off}$, $V_{-1}$, and $V_-$ are controlled by the microprocessor of FIG. 2. The selected value of the $V_{on}$, $V_{off}$, $V_-$, and $V_-$ depend upon the structure of the cavity and the working infrared wavelength. Preferably, the selected value is comparable with the used CMOS circuits and used microprocessor.

Figure 7:
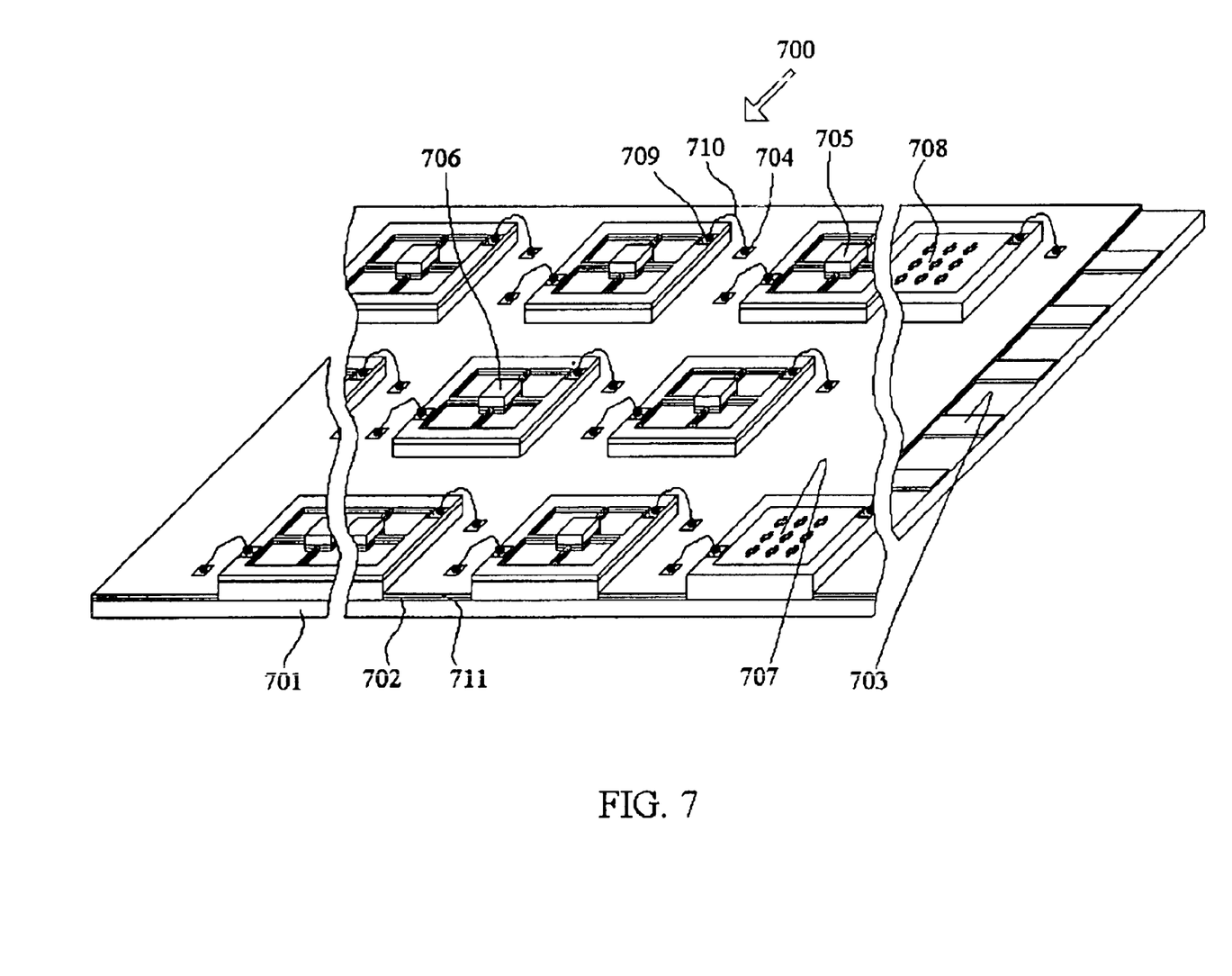
FIG. 7 shows a sub-assembly incorporating a micromachined infrared spectrometer array with a driver circuit and a micromachined infrared tunable filter with a driver circuit.

As shown in FIG. 7, a first sub-assembly board 700 consists of a micromachined infrared mechanical modulator array 705, a micromachined infrared tunable filter 706, a driver circuit 707 for the modulator array 705, and a driver circuit 708 for the tunable filter 706, which are mounted on the surface of a glass plate 701 by chip bonding. An electrical connection pattern is formed on the surface of the glass plate 701, which includes bonding pads 704 and input/output ports 703. The connection pattern is covered by a dielectric layer 702 and an infrared blocking layer 711. The modulator array 705, tunable filter 706, driver circuits 707 and 708 are connected to the connection pattern through bonding pads 709 and bonding wires 710. The control signal and power signal are delivered to the modulator array 705, tunable filter 706, driver circuits 707 and 708 through the input/output ports 703.

Figure 8:
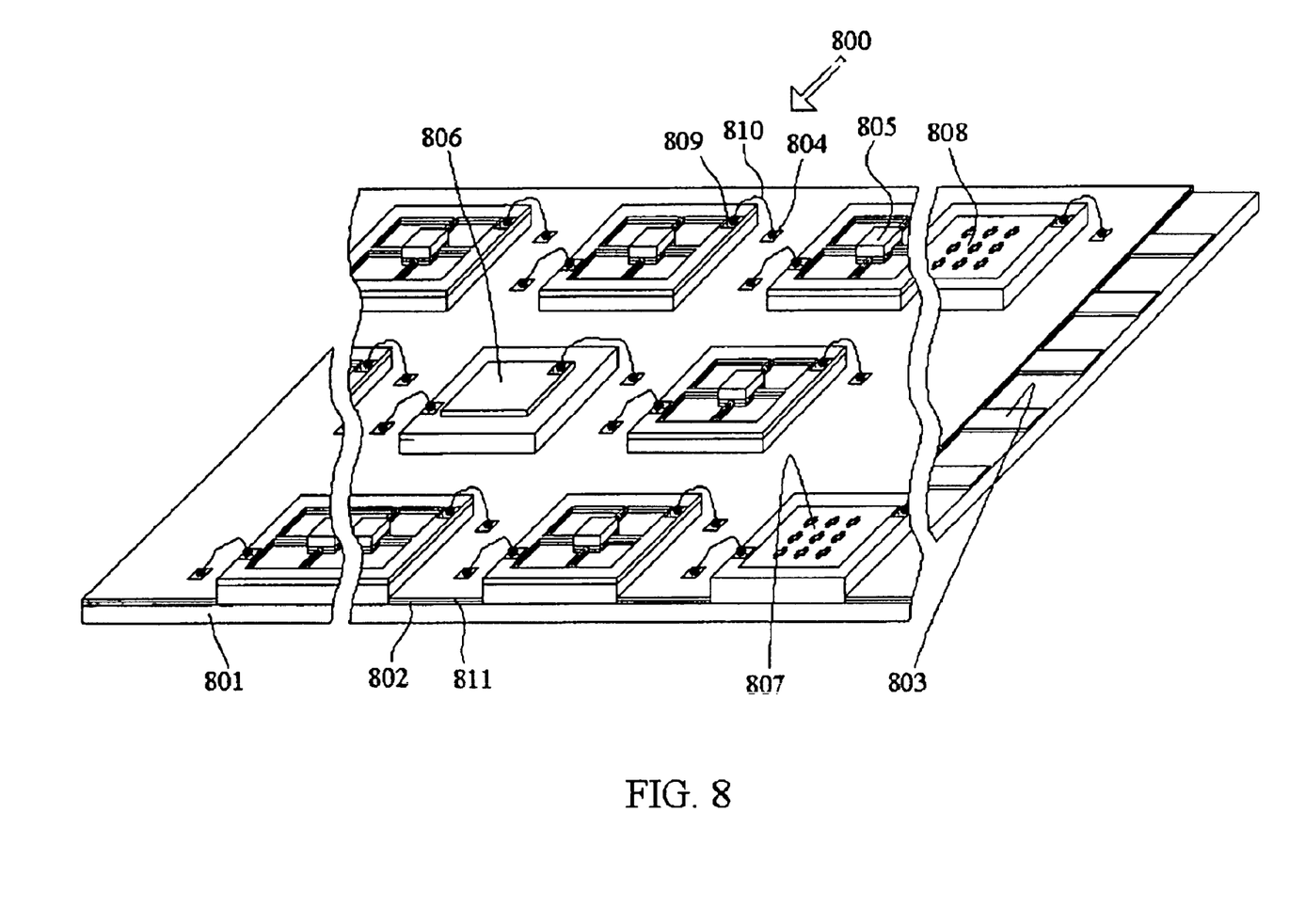
FIG. 8 shows a sub-assembly incorporating a micromachined infrared mechanical-modulator array with a driver circuit and an infrared detector with a signal processing circuit.

As shown in FIG. 8, a second sub-assembly board 800 consists of a micromachined infrared spectrometer array 805, an infrared detector 806, a driver circuit 806 for the spectrometer array 805, and a synchronous detection circuit 808 for the infrared detector 806, which are mounted on the surface of a glass plate 801 by chip bonding. An electrical connection pattern is formed on the surface of the glass plate 801, which includes bonding pads 804 and input/output ports 803. The connection pattern is covered by a dielectric layer 802 and an infrared blocking layer 811. The spectrometer array 805, infrared detector 806, driver circuits 807 and synchronous detection circuit 808 are connected to the connection pattern through bonding pads 809 and bonding wires 810. The control signal and power signal are delivered to the spectrometer array 805, infrared detector 806, driver circuits 807 and synchronous detection circuit 808 through the input/output ports 803.

In near infrared the infrared detector 806 can be a lead sulfide (PbS) sensor or a lead selenide (PbSe) sensor. Sensors PbS and PbSe are chemically deposited, thin film, photoconductive IR detectors that require a bias voltage to measure resistance drop when exposed to IR radiation. It is important to note that virtually all PbS/PbSe characteristics vary with temperature. Detectors also exhibit typical 1/f noise. For optimum performance, detector temperature should be stabilized and incident radiation should be chopped.

In mid-infrared the infrared detector 806 is preferably a micromachined thermopile formed on a silicon nitride membrane. The hot junctions of the gold-polysilicon thermocouples are located in the central region of the membrane, while the cold junctions are located on the thick silicon rim. Efficient thermal isolation, small size, and a large number of integrated junctions can result in high sensitivity and high-speed detection of the infrared light.

Thermopiles typically operate over a broad temperature range (including room temperature) and are insensitive to drifts in substrate temperature, so that it is not necessary to provide for either cooling or stabilization of temperature. Thermopiles are passive devices that generate voltage outputs, without need to supply bias voltage. Thus, in comparison with other infrared detectors in the same class, thermopiles consume less power and can be supported by simpler readout circuits. Moreover, if thermopiles are read out with high-input-impedance amplifiers, they exhibit negligible 1/frequency noise because there is negligible readout current. Moreover, thermopiles typically exhibit highly linear response over many orders of magnitude of incident infrared power.

A commercial thermopile is made with n-doped polysilicon and Al using a quasi-standard CMOS process. The membrane consists of an 800-nm sandwich of low-pressure chemical-vapor-deposited $SiO_2/Si_3N_4$ on top of a 400-$\mu$m-thick silicon chip, which is anisotropically etched with KOH at 85° C. The typical time constant is about 10 ms.

The micromachined thermopile can be replaced by an un-cooled micromachined bolometer. Such bolometer is formed on a suspended a dielectric membrane with a central square pad and two long supporting legs. The bolometer uses Pt or $VO_2$ as a resistor material. The formed resistor is covered with an absorber. A commercial bolometer uses a $SiO_2$ layer to form the dielectric membrane. The size of the bolometer is 1.5 mm by 1.5 mm. The resistor's measure is 50 $\mu$m by 50 $\mu$m. This bolometer can be modulated up to 100 Hz.

In near infrared the infrared light source preferably utilizes a metal wire source such as a tungsten-halogen lamp. But in mid-infrared the infrared light source preferably utilizes a thin film source.

According to Stefan-Boltzmann law, the total radiant flux emitted from a surface of a blackbody can be expressed in the form $M_{bb}=\sigma T^4$, where $M_{bb}$ is the exitance of the emitter surface in a vacuum, $\sigma$ is the Stefan-Boltzmann constant, and T is the temperature in degrees Kelvin. The relationship between the emitted peak wavelength $\lambda_m$ and the temperature T can be expressed by Wien law, in form $\lambda_m T=b$, where b is the Wien constant.

It can be seen that for a thermal radiator utilizing metal wire or metal foil would have a very low total radiant flux, because its emission temperature is very low. In order to obtain higher total radiant flux, a thermal radiator utilizing thin film sources is preferred. The films must have sufficient resistivity (>150 $\mu$-cm) for making heaters of controllable thickness. The most popular materials that are currently in use for thin film heaters include sputtered Ta—Al alloys, heavily doped silicon and sputtered $HfB_2$.

Figure 9:
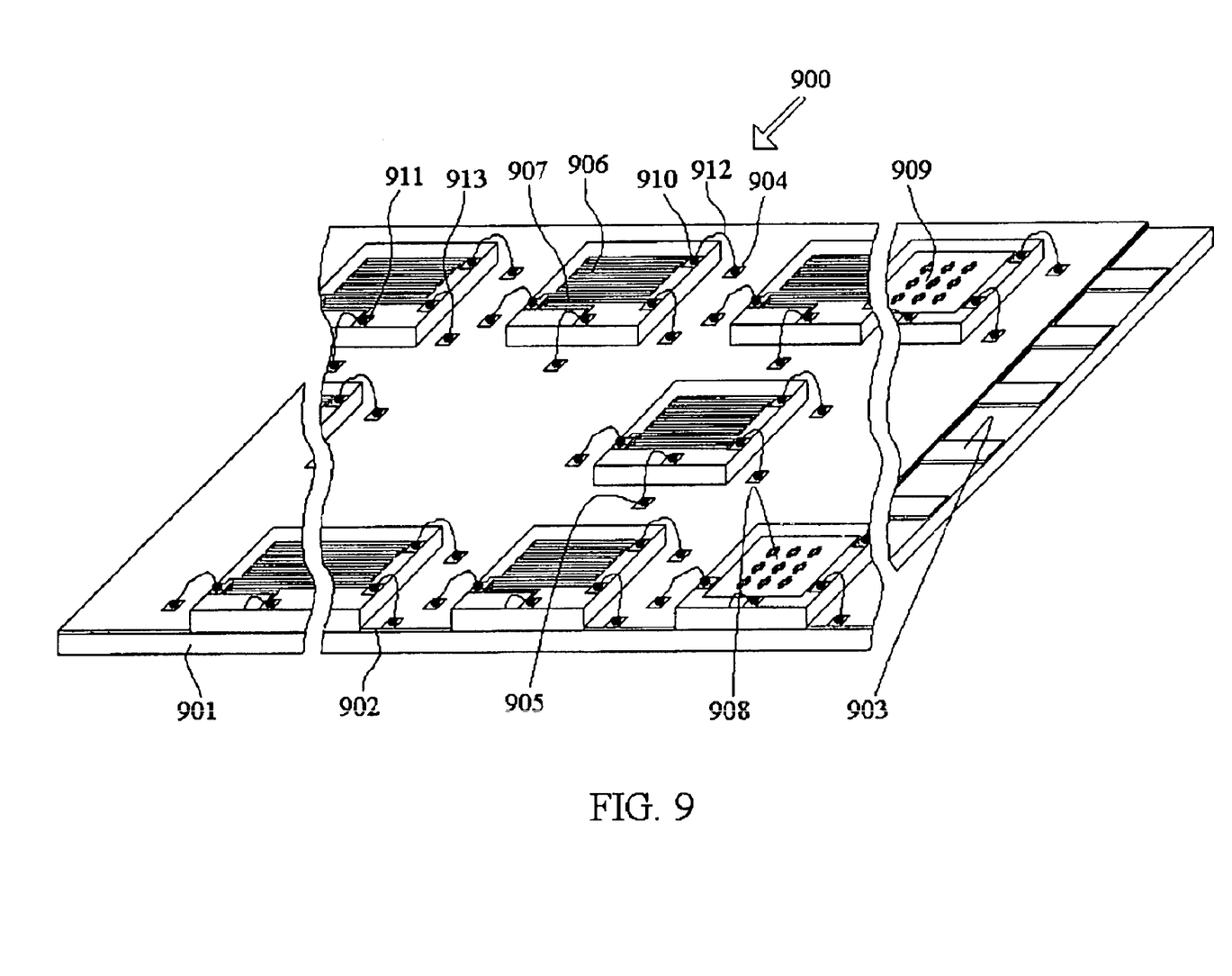
FIG. 9 shows a sub-assembly incorporating an infrared thermal radiator array, a temperature sensor array, and a signal processing circuit used for temperature sensors and a power supply circuit used for the infrared thermal radiator.

FIG. 9 shows a third sub-assembly board 900 consists of a silicon chip array each incorporating a thermal radiator 906 and temperature sensor 907 thereon. The silicon chip array is chip-bonded on the surface of a glass plate 901. The glass plate 901 also incorporates two circuit chips 908 and 909 for processing the signals of the thermal radiators 906 and temperature sensors 907, respectively. An electrical connection pattern is formed on the surface of the glass plate 901, which include a plurality of bonding pads 904 and 905, and input/output ports 903. A dielectric layer 902 is used to cover the electrical connection pattern. All chips are electrically connected to each other through bonding pads 910 and bonding wires 912.

A commercial thermal radiator consists of three main blocks: mechanical support, heater and substrate. The mechanical support uses a $Si_3N_4$ membrane of 1 μm thickness disposed on a silicon substrate. The size of the $Si_3N_4$ membrane is 100 μm×100 μm, which is supported by six micro bridges of 150 μm length and 10 μm width. The heater is formed of a 2000 Å thick sputtered NiCr stripe. Fine wires of copper are attached to the opposing edges of the NiCr stripe. Titanium (150 Å thickness) followed by Gold (2000 Å thickness) is deposited on the NiCr stripe along the current-injecting edges to homogenize the electrical field and reduce current densities at the injection point. During operation the heater generates photons within a specific Planck Function band-pass that depends on the final temperature of the heater.

Figure 10:
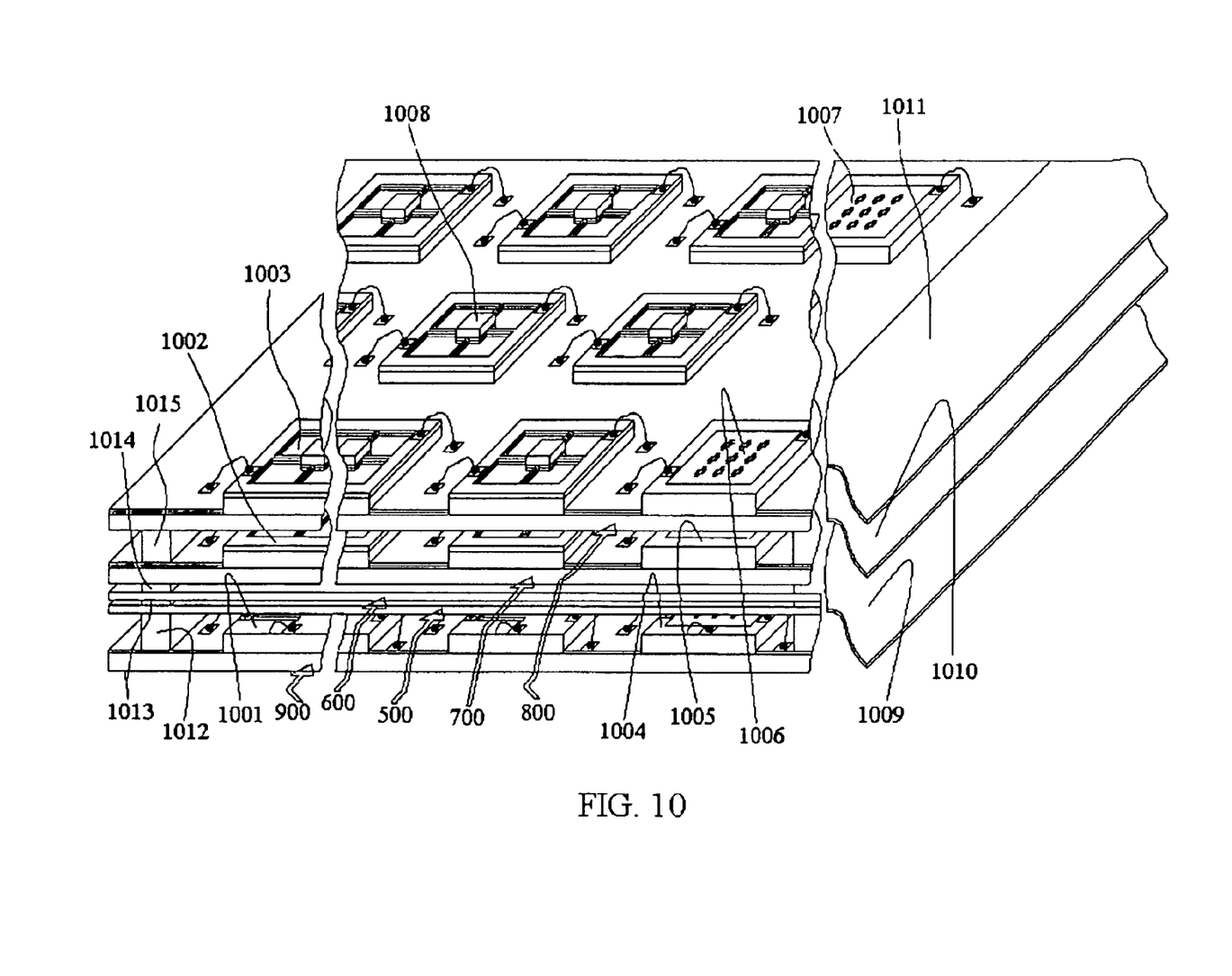
FIG. 10 shows an assembly incorporating a micromachined infrared spectrometer array with a driver circuit, a micromachined infrared mechanical-modulator array with a driver circuit, a micromachined infrared tunable filter with a driver circuit, a micromachined infrared detector with a signal processing circuit, an infrared band pass filter, an infrared thermal radiator array with a temperature sensing circuit and a power supply circuit.

A more detailed perspective view of the assembly of a non-invasive blood glucose monitor, according to the present invention, is shown in FIG. 10. As can be seen in the FIG. 10. The monitor is constructed by incorporating the first sub-assembly board 700, a second sub-assembly board 800, a third sub-assembly board 900, a collimator array 500, and a narrow band filter 600. The board 800 faces the surface of the measured blood subject. It can be seen that the board 900 contains an infrared source chip 1001 consisting of a thermal radiator and a temperature sensor, a circuit chip 1004 for driving the thermal radiators, and an adaptor 1009 for connecting the board 900 to the microprocessor of the monitor. The board 700 contains a cavity chip 1002 consisting of an infrared spectrometer, a circuit chip 1005 for driving the infrared spectrometers, and an adaptor 1010 for connecting the board 700 to the microprocessor of the monitor. The board 800 contains a cavity chip 1003 consisting of an infrared mechanical modulator, a cavity chip 1008 consisting of an infrared tunable filter, a circuit chip 1006 for driving the infrared spectrometers, a circuit chip 1007 for driving the infrared tunable filter, and an adaptor 1011 for connecting the board 800 to the microprocessor of the monitor. All the boards are mounted together through bonding bumps 1012, 1013, 1014, and 1015 so that each optical filter of the optical filter array is aligned with a thermal radiator of the thermal radiator array on the back side and a mechanical modulator of the mechanical modulator array on the front side, and the tunable filter is aligned with the infrared detector on the front side. In this configuration the path for delivering the infrared light starts from the surface of the thermal radiator, then passes through the collimator, the narrow band filter, a spectrometer, and a modulator, finally ends at the surface of the blood subject. The path for delivering back-diffused infrared light starts from the surface of the blood subject, then passes through the tunable filter, finally ends at the surface of the detector Although the invention has been described herein with reference to certain preferred embodiments, one skilled in the art will readily appreciate that other applications may be substituted without departing from the spirit and scope of the present invention. Accordingly, the invention should only be limited by the claims included below.

What is claimed is:

1. A micro-optical-mechanical-electro-system (MOMES)-based non-invasive blood glucose monitor comprising:

a micromachined infrared optical filter array each for continuously dividing an infrared light in a wavelength range within 0.8 to 25 micron from an infrared light, a micromachined infrared mechanical modulator array each for turning the infrared light into an alternating infrared light, at least one micromachined infrared tunable filter for selecting back-diffused alternating monochromatic infrared light emitted from a measured blood subject that is illuminated by the alternating infrared light, three driver circuits for actuating the optical filter array, mechanical modulator array, and tunable filter, respectively, at least one infrared detector for converting the back-diffused alternating monochromatic infrared light into an alternating electronic signal, at least one infrared light source for irradiating the infrared light, at least one collimator enabling the incoming infrared light to run parallel to its optic axis, and a photo-integrated circuit (IC) combining with the infrared detector for synchronous detection and amplification of the electronic signal generated by the synchronous detection.

2. The MOMES-based non-invasive blood glucose monitor as claimed in claim 1, further comprising:

an infrared band pass filter for selecting an infrared light in a wavelength range within 0.8 to 25 micron, a data processing circuit consisting of an analog multiplexer circuit, a sample-and-hold circuit, and an analog to digital converter for providing a digital output, and a microprocessor for determining the glucose concentration of the measured blood subject.

3. The MOMES-based non-invasive blood glucose monitor as claimed in claim 1, wherein each of said micromachined infrared optical filter array, each of said micromachined infrared mechanical modulator array, and said micromachined infrared tunable filter respectively consists of an air gap variable Fabry-Perot cavity that is defined by two parallel planar reflectors.

4. The MOMES-based non-invasive blood glucose monitor as claimed in claim 1, wherein said infrared light source is a metal wire or metal foil lamp.

5. The MOMES-based non-invasive blood glucose monitor as claimed in claim 1, wherein said infrared light source is a thin film radiator array.

6. The MOMES-based non-invasive blood glucose monitor as claimed in claim 1, wherein said infrared detector is a photoconductive sensor.

7. The MOMES-based non-invasive blood glucose monitor as claimed in claim 1, wherein said infrared detector is a micromachined thermopile.

8. The MOMES-based non-invasive blood glucose monitor as claimed in claim 1, wherein said infrared detector is a micromachined bolometer.

9. A micro-optical-mechanical-electro-system (MOMES)-based infrared device assembly for a non-invasive blood glucose monitor comprising:

a micromachined infrared optical filter array each for continuously dividing an infrared light in a wavelength range within 0.8 to 25 micron from an infrared light, a micromachined infrared mechanical modulator array each for turning the infrared light into an alternating infrared light, at least one micromachined infrared tunable filter for selecting back-diffused alternating monochromatic infrared light emitted from a measured blood subject that is illuminated by the alternating infrared light, three driver circuits for actuating the optical filter array, mechanical modulator array, and tunable filter, respectively, at least one infrared detector for converting the back-diffused alternating monochromatic infrared light into an alternating electronic signal, at least one infrared light source for irradiating the infrared light, at least one collimator enabling the incoming infrared light to run parallel to its optic axis, and a photo-integrated circuit (IC) combining with the infrared detector for synchronous detection and amplification of the electronic signal generated by the synchronous detection.

10. The MOMES-based infrared device assembly for a non-invasive blood glucose monitor as claimed in claim 9, wherein each of said micromachined infrared optical filter array, each of said micromachined infrared mechanical modulator array, and said micromachined infrared tunable filter respectively consists of an air gap variable Fabry-Perot cavity that is defined by two parallel planar reflectors.

11. The MOMES-based infrared device assembly for a non-invasive blood glucose monitor as claimed in claim 9, wherein said infrared light source is a metal wire or metal foil lamp.

12. The MOMES-based infrared device assembly for a non-invasive blood glucose monitor as claimed in claim 9, wherein said infrared light source is a thin film radiator array.

13. The MOMES-based infrared device assembly for a non-invasive blood glucose monitor as claimed in claim 9, wherein said infrared detector is a photoconductive sensor.

14. The MOMES-based infrared device assembly for a non-invasive blood glucose monitor as claimed in claim 9, wherein said infrared detector is a micromachined thermopile.

15. The MOMES-based infrared device assembly for a non-invasive blood glucose monitor as claimed in claim 9, wherein said infrared detector is a micromachined bolometer.

16. A micro-optical-mechanical-electro-system (MOMES)-based non-invasive blood glucose measurement method comprising steps:

actuating one of a micromachined infrared optical filter array for continuously dividing an infrared light in a wavelength range within 0.8 to 25 micron from an infrared light source, actuating one of a micromachined infrared mechanical modulator array for turning the infrared light into an alternating infrared light, actuating at least one micromachined tunable filter for selecting back-diffused alternating monochromatic infrared light emitted from a measured blood subject that is illuminated by the alternating infrared light, using at least one infrared detector to convert the back-diffused alternating monochromatic infrared light into an alternating electronic signal, and performing synchronous detection of the alternating electronic signal and amplification of the electronic signal generated by the synchronous detection.

17. The MOMES-based non-invasive blood glucose measurement method as claimed in claim 16, wherein each of said micromachined infrared optical filter array, each of said micromachined infrared mechanical modulator array, and said micromachined infrared tunable filter respectively consists of an air gap variable Fabry-Perot cavity that is defined by two parallel planar reflectors.

18. The MOMES-based non-invasive blood glucose measurement method as claimed in claim 16, wherein said infrared light source is a metal wire or metal foil lamp.

19. The MOMES-based non-invasive blood glucose measurement method as claimed in claim 16, wherein said infrared light source is a thin film radiator array.

20. The MOMES-based non-invasive blood glucose measurement method as claimed in claim 16, wherein said infrared detector is a photoconductive sensor.

21. The MOMES-based non-invasive blood glucose measurement method as claimed in claim 16, wherein said infrared detector is a micromachined thermopile.

22. The MOMES-based non-invasive blood glucose measurement method as claimed in claim 16, wherein said infrared detector is a micromachined bolometer.

* * * * *